United States Patent [19]
Brown

[11] Patent Number: 5,520,882
[45] Date of Patent: May 28, 1996

[54] DENTAL HANDPIECE HYGIENIC PHARMACEUTICAL STERILIZATION LUBRICANT

[76] Inventor: Kenneth R. Brown, 7127 E. Becker Ln., #77, Scottsdale, Ariz. 85254

[21] Appl. No.: 283,851

[22] Filed: Aug. 1, 1994

[51] Int. Cl.⁶ .................................................. C23F 11/00
[52] U.S. Cl. ........................ 422/7; 252/10; 422/1; 422/26; 422/27; 422/28; 422/40; 433/104
[58] Field of Search ................... 433/104; 422/1, 422/26, 27, 7, 28, 40; 252/10

[56] References Cited

U.S. PATENT DOCUMENTS

| | | | |
|---|---|---|---|
| 4,218,216 | 8/1980 | Sugai et al. ........................... | 433/104 |
| 4,920,107 | 4/1990 | Pera et al. ............................. | 422/1 X |
| 5,131,845 | 7/1992 | Feldman et al. ....................... | 433/104 |
| 5,283,005 | 2/1994 | Nelson, Jr. et al. ................... | 422/1 X |

*Primary Examiner*—Robert J. Warden
*Assistant Examiner*—Krisanne M. Thornton
*Attorney, Agent, or Firm*—Donald J. Lisa

[57] ABSTRACT

About ½ cc of a sterile composition (5) dropped into the rotor drive air feed line (11) of a dental handpiece (10) while holding the handpiece upside down protects and lubricates the handpiece bearings and turbine during the subsequent auto-clave sterilization process. An additional dosage inserted into the bur hole after the auto-clave process further lubricates the handpiece and inhibits rust from forming on the handpiece bearings and turbine during use. The pre-sterilization dosage and post-sterilization dosage of measured amounts may be separately packaged in disposable capsules (20, 30). The composition (5) is made by heat mixing until sterile about 10% by volume of a sterile solution of Power-Up™ NNL-690, which is a liquid hydrocarbon boundary lubricant; and corrosion inhibitor, with 90% by volume of pharmaceutical grade mineral oil.

30 Claims, 2 Drawing Sheets

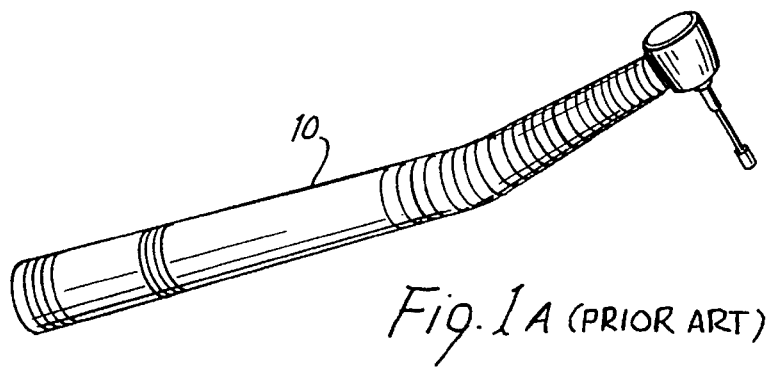
Fig. 1A (PRIOR ART)
Fig. 1B (PRIOR ART)
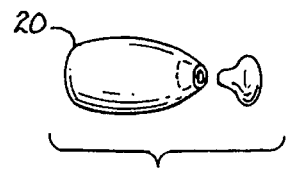
Fig. 1C (PRIOR ART)
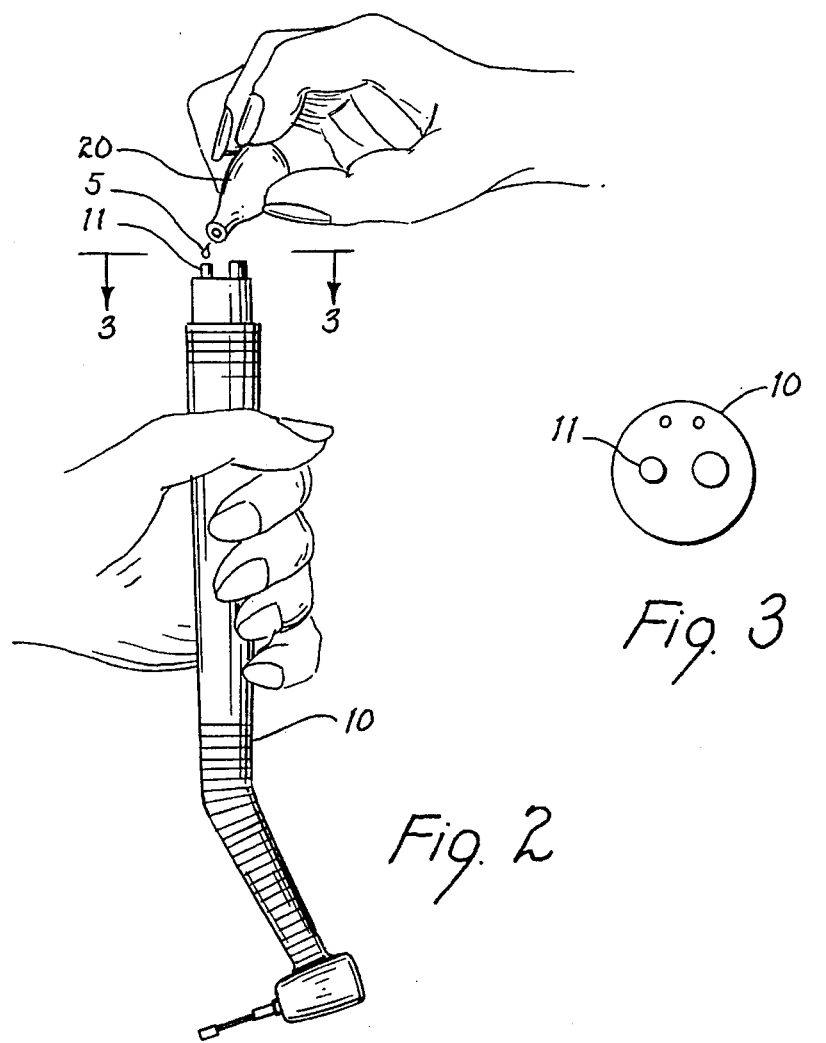
Fig. 2
Fig. 3

DENTAL HANDPIECE HYGIENIC PHARMACEUTICAL STERILIZATION LUBRICANT

BACKGROUND OF THE INVENTION

Field of the Invention

The present invention relates generally to a sterile, pharmaceutical composition inserted into a dental handpiece prior to and after sterilization to lubricate moving parts and to inhibit handpiece corrosion, and, more particularly, to the process of sterilizing such instruments by inserting such compositions prior to auto-claving.

a. Prior Handpiece Lubricants and Processes

It is well known that a dental handpiece has to be lubricated periodically to maintain its efficiency and prevent premature failure. The rotor or turbine in the handpiece is supported in bearings which are subjected to severe wear due to the wide range of speeds and torque loads involved in drilling teeth. Typically, the bearings are lubricated by adding oil in a variety of ways, such as from a large oiler connected to the rotor drive air feed line which intermittently drops oil into the inlet air stream where the oil is atomized and then carried to the rotor entrained in the inlet air.

In a method disclosed in Sugai U.S. Pat. No. 4,218,216 an improved system employed a small oiler inserted in the air feed line having a spring loaded check valve overcome by feed air pressure to allow oil to escape into the feed air, be atomized and continuously lubricate the rotor bearings. However, with the onset of AIDS and the need for increased sterilization, such a system did not function during auto-claving and offered no protection against cross contamination.

By 1991, as disclosed in Feldman U.S. Pat. No. 5,131,845, it was highly recommended that the handpiece be sterilized frequently, and sterilization of the handpiece between patients was becoming a recommended procedure. However, increased sterilization required more frequent lubrication. It was known to lubricate the handpiece both before and after sterilization.

However, the initial lubricants used pre-sterilization and post-sterilization were generally the same products as were previously available prior to the need for increased sterilization. These products did not survive the heat of the auto-clave process itself and were ineffective. Handpiece failures increased and were replaced at an average unit cost of about $150.00.

While Feldman developed an improved method of inserting the oil into the rotor drive air feed line using a squeezable sealed capsule containing the lubricant and his system further prevented the transmission of viral and bacterial matter to the patient and the dentist, it did not advance the art of developing lubricant compositions that could not only withstand the auto-clave cycle, but also, protect the handpiece during the auto-clave cycle by retaining and/or enhancing their boundary lubricating and anti-corrosion characteristics. Feldman merely disclosed that his shell 10 was filled with an extremely light, dental grade, FDA approved, lubricating oil which was required for the handpiece and widely used in the art. Feldman 7:21–24.

b. Industrial Product Preservatives

It was also known to add ingredients, such as, an anion selected from the group consisting of sulfate, acetate and citrate groups, to aqueous industrial products to inhibit microbiological degradation in such products resulting from the growth of micro-organisms which can cause odors, deterioration and corrosion. Pera U.S. Pat. No. 4,920,107. In an improvement to Nelson U.S. Pat. No. 5,283,005, the biocidal efficacy of such additives were enhanced by mixing a known preservative (pyrithione, used in lubricants) with a known antibiotic (lipopeptide, for treating superficial infections) to inhibit notably bacteria and fungi from forming in the composition itself when used alone or in combination with an inert carrier, such as water, liquid hydrocarbons, ethanol, isopropanol, or the like. 2:63–67. However, there was no disclosure or suggestion of the composition of the present invention, that the disclosed compositions were sterile or could be used as pre-sterilization lubricants for a dental handpiece, or that the boundary lubricating or protective quality of the compositions were enhanced.

c. Boundary Lubricant Theory

The general theory of how a boundary lubricant works is well known. When surfaces contact each other during rolling or sliding contact, wear particles are formed which combine with the lubricant to form an eutectic film (the new material has a lower melting point than the original material) which can withstand high loads and become the sacrificial layer which is worn away and removed instead of the underlying (rotor/bearing) material, thus, reducing friction.

It is an object of the present invention to provide a new, low coefficient of friction, lubricant composition and process that allows insertion of the composition into the rotor drive air inlet prior to the auto-clave cycle, or after, or both, and which remains effective during the auto-clave cycle and thereafter to provide improved protection of the handpiece against corrosion, substantially reduced wear rates and substantially improved resistance to wear, thereby extending significantly the service life of the handpiece.

It is a further objective of the present invention to provide a new sterile composition and process that reduces the risk of cross contamination from viruses and bacteria.

SUMMARY OF INVENTION

Set forth below is a brief summary of the invention in order to achieve the foregoing and other benefits and advantages in accordance with the purpose of the present invention as embodied and broadly described herein.

One aspect of the present invention is a dental handpiece lubricant which includes a composition of about 90% by volume of a liquid hydrocarbon and about 10% by volume of a boundary lubricant and corrosion inhibitor. This composition is made by mixing about 10% by volume of a solution of NNL-690 with about 90% by volume of a pharmaceutical grade mineral oil. Preferably, the NNL-690 solution is initially heated until it is hygienic, that is, sterile and the final composition is preferably additionally heated at about 225° F. for about one hour or until sterile and thoroughly mixed.

A further aspect of the present invention is the process of sterilizing a dental handpiece having a rotor supported in a bearing and a bur hole adapted to receive and hold a bur by lubricating the handpiece rotor and bearing by inserting a predetermined amount of the aforesaid composition into the rotor drive air feed line while holding the handpiece vertically upside down, and, then, auto-claving the handpiece in a sealed plastic bag.

A further aspect of the invention is protecting the handpiece in use by inserting a predetermined amount of the aforesaid composition into the bur hole before each use or during use.

DESCRIPTION OF THE DRAWINGS

FIG. 1A is a perspective view of a handpiece of the prior art.

FIG. 1B is a perspective view of a disposable capsule of the prior art in which the composition of the present invention may be conveniently packaged.

FIG. 1C is a perspective view of the capsule of FIG. 1B with the head detached.

FIG. 2 is a front elevation of the handpiece of FIG. 1A held vertically upside down and showing the capsule of FIG. 1C containing the composition of the present invention being squeezed to insert a measured dosage of the composition into the air feed inlet passage of the handpiece prior to sterilization.

FIG. 3 is a top elevation of FIG. 2.

DETAILED DESCRIPTION OF THE PREFERRED EMBODIMENT

Figures 4, 5:
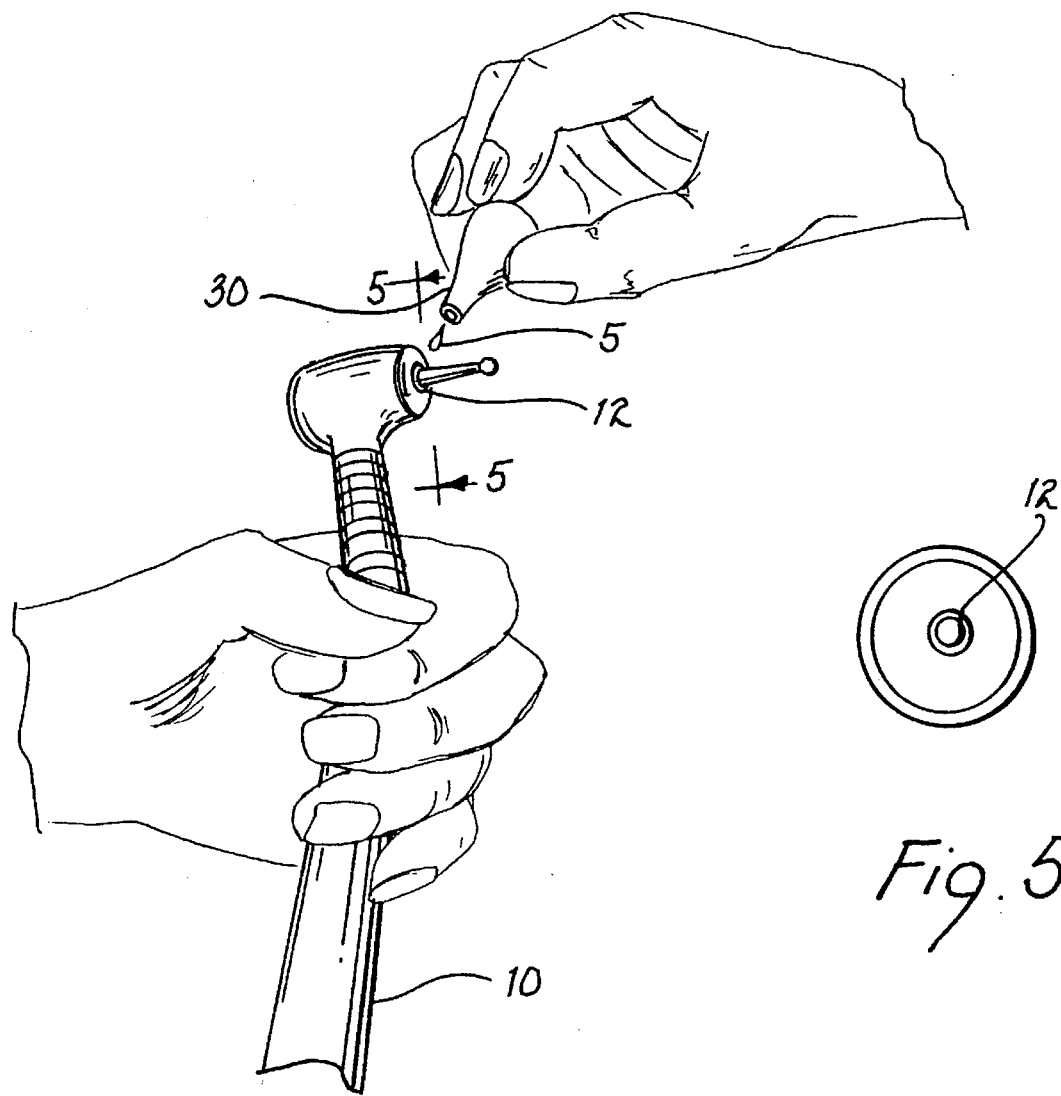
FIG. 4 is a front perspective of the handpiece of FIG. 1A held right side up and slightly at an angle and showing the capsule of FIG. 1C containing the composition of the present invention being squeezed to insert, after sterilization, a measured amount of the composition into the bur hole of the handpiece head which houses the turbine, the turbine bearings and the chuck which holds the bur.
FIG. 5 is a right side elevation of FIG. 4.

The composition of the present invention is a specially formulated, mineral based, hygienic, pharmaceutical lubricant. It may be packaged individually for use prior to sterilization of the handpiece without risk of contamination by the lubricant itself. It may be packaged individually for use after sterilization of the handpiece without risk of contamination by the lubricant itself. The pre-sterilization package contains a measured amount of about ½ cc, enough for one application. The post-sterilization package contains a pre-measured amount of about ten (10) applications of about 2 drops each.

The composition 5 of the present invention comprises a mixture of liquid hydrocarbons refined from petroleum including about 90% by volume of a fully refined, pharmaceutical grade, non-sterile, white mineral oil to which has been added and thoroughly mixed about 10% by volume of a fully refined, light, mineral based oil, amber in color, as a boundary lubricant enhancer and corrosion inhibitor. The composition 5 is manufactured for applicant by Petroleum Products of America of Scottsdale, Az. and is sold under applicant's brand name STERI-LUBE™.

The mineral oil used in the present invention meets the requirements of the United States Pharmacopeia XXII, as well as the requirements of the Food and Drug Administration per 21 C.F.R. § 172.878.

The boundary lubricant enhancer and corrosion inhibitor of the present invention is a non-sterile petroleum product known by applicant by the Power-Up™ designation NNL-690 ("NNL-690"), made by Power-Up, Inc. and sold by Power-Up Distribution, Inc. both of 6173-6 Street SE, Calgary, AB, Canada T2H1L9 ("Power-Up"). NNL-690 is a boundary lubricant comprising a solution of the following ingredients:

| CAS NO. | APPROX % WT. | CHEMICAL NAMES |
|---|---|---|
| 60-92-4 | 0.08 | Adenosine 3',5'-Cycho-Monophosphate |
| 106282-86-4 | 18.0 | C22–C40, Chlorinated Paraffin |
| 68837-40-6 | 1.1 | Aromatic Amino Phosphate |
| 128-87-0 | 0.02 | Butylated Hydroxytoluene |
| 61789-86-4 | 1.2 | Calcium Alkylsulfonate |
| 149-57-5 | .5 | Calcium Naphthenate |
| 83-67-0 | 0.1 | 3.7 Dimethylxanthine |
| No Cas # | 3.0 | Glycerol Monooloate |
| 64742-46-7 | 23.0 | Isoparaffinic Hydrocarbon |
| 8006-54-0 | 2.4 | Lanolin |
| 7683-64-9 | 12.0 | Squalene |
| 67-03-8 | 2.3 | Thiamine |
| 8042-47-5 | 36.0 | White Mineral Oil |
| No Cas # | 0.3 | Methylene-Dibutyldithiocarbamate |

While Power-Up has limited public distribution of the specific composition of NNL-690 to selected ones of its customers, the NNL-690 formula has not been maintained as a trade secret. Moreover, the product is readily commercially available to any buyer and may be obtained by simply contacting Power-Up at the above location. Prior to the present invention, it has been known to use NNL-690 as a boundary lubricant enhancer to reduce friction in automotive engines. Preferably, the enhancer/inhibitor solution of the present invention is first heated to sterilize it. The lubricant enhancer/inhibitor used in the present invention also complies with the Material Safety Data Sheet ("MSDS") specifications.

The final lubricant composition 5 of the present invention is made by mixing the 90% by volume mineral oil with the 10% by volume enhancer/inhibitor and then heating the final mixture to sterilize it and assure a complete mixing of the ingredients.

Additional characteristics of the final composition 5 of the present invention are as follows:
1. Color/odor: Clear—Pleasant, nutty order.
2. Specific Gravity: <1.0@15 Deg. C.
3. Vapor Pressure: <0.5 mm
4. Evaporation Rate: Nil@25 Deg. C.
5. Boiling Point: >230 Deg. C.
6. Pour Point: >–9 Deg. C.
7. Flash Point: 193. Deg. C.; >380 Deg. F.
8. Solubility in Water: Nil.
9. pH: N/A.
10. Viscosity: 100 (SUS)

WORKING EXAMPLE

Take 5.5 gallons of NNL-690 and heat. Mix the resulting liquid with 49.5 gallons of mineral oil and heat again. The two heating steps may be omitted if a sterile final composition is not required. Package and ship.

The packaging of the invention is conventional. A pre-sterilization package, such as a capsule 20, may be conveniently sized to hold an amount of the final composition of the present invention sufficient to protect the handpiece 10 during the sterilization process, such as, about ½ cc. A post-sterilization package, such as a capsule 30, may be conveniently sized as a 1 cc reclosable applicator holding ten individual applications of about 1/10th cc each. 1/10th cc is the equivalent of about 2 drops. The post-sterilization capsule will be a reclosable container as is well known in the art.

PROCESS OF USING

The process of using the composition of the present invention is best understood with reference to the drawings.

1. FIG. 1. shows the handpiece 10 of the prior art. The handpiece 10 is held vertically upside down as shown in FIG. 2. The cap of the capsule 20 containing the sterile pre-auto-clave composition 5 is removed and the capsule is squeezed to allow a dosage of about ½ cc of the lubricant to enter the main air hole 11 of handpiece 10.

2. Place the handpiece 10 in a sterilization bag (not shown) and place the bag into a standard auto-clave (not shown).

3. Follow the auto-clave instructions.

4. When the auto-clave cycle is complete, remove the bag and handpiece.

5. As seen in FIG. 2 hold the handpiece 10 right side 18 up and at an angle to expose access to the bur hole 12 and then squeeze capsule 30 allowing two (2) drops of the sterile post-auto-clave solution 5 to enter into bur hole 12 before use of handpiece 10.

The foregoing description of a preferred embodiment and best mode of the invention is known to applicant at the time of filing the application, and has been presented for the purpose of illustration and description. It is not intended to be exhaustive or to limit the invention to the precision form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications suited to the particular use contemplated. It is intended that the scope of the invention be defined by the claims appended hereto.

I claim:

1. The process of sterilizing a dental handpiece comprising the steps of:

(a) providing a rotor supported in a bearing and having a bur hole adapted to receive and hold a bur, (b) lubricating the rotor and bearing of the handpiece with a predetermined amount of a composition comprising a solution of about 90% by volume of a liquid hydrocarbon and about 10% by volume of a boundary lubricant and corrosion inhibitor, and (c) inserting the handpiece into a sealed bag and subjecting the bag to an auto-clave cycle sufficient to sterilize the handpiece.

2. The process of claim 1 wherein the predetermined amount is about ½ cc.

3. The process of claim 1 wherein the lubricating step further comprises the step of inserting the composition into a rotor drive air feed line while holding the handpiece vertically upside down.

4. The process of claim 1 wherein the composition of the lubricating step further comprises:

the boundary lubricant and corrosion inhibitor is NNL-690, and the liquid hydrocarbon includes a pharmaceutical grade mineral oil.

5. The process of claim 4 wherein the composition is sterile.

6. The process of claim 5 further comprising the step of:

after completing the auto-clave cycle, inserting a predetermined amount of the composition into the bur hole.

7. The process of claim 4 wherein the composition includes not more than about 10% by volume of NNL-690 and not less than about 90% by volume of the liquid hydrocarbon.

8. The process of claim 1 further comprising the step of:

after completing the auto-clave cycle, inserting a predetermined amount of the composition into the bur hole.

9. The process of protecting a dental handpiece having a rotor supported in a bearing and a bur hole constructed and arranged to receive and hold a bur comprising the step of:

lubricating the rotor and bearing of the handpiece with a predetermined amount of a composition comprising about 10% by volume of NNL-690 and about 90% by volume of a pharmaceutical grade mineral oil.

10. The process of claim 9 wherein the composition comprises not more than about 10% NNL-690 and not less than about 90% mineral oil.

11. The process of claim 10 wherein the predetermined amount is about 2 drops.

12. The process of claim 9 wherein the composition is sterile.

13. The process of claim 9 wherein the lubricating step further comprises the step of inserting the composition into the bur hole.

14. The process of claim 1 wherein the lubricating step further comprises the step of:

lubricating with a composition which includes vitamin E as a rust inhibitor.

15. The process of claim 9 wherein the composition further comprises vitamin E as a rust inhibitor.

16. The process of making a dental handpiece lubricant comprising the step of:

mixing about 10% by volume of NNL-690 and about 90% by volume of a pharmaceutical grade mineral oil.

17. The process of claim 16 further comprising the step of:

heating the mixture until sterile.

18. The process of claim 16 wherein the mixture comprises not more than about 10% by volume of NNL-690 and not less than about 90% by volume of mineral oil.

19. The process of claim 16 wherein the NNL-690 comprises a liquid hydrocarbon boundary lubricant and corrosion inhibitor.

20. A dental handpiece lubricant comprising a mixture of about 10% by volume of NNL-690 and about 90% by volume of a pharmaceutical grade mineral oil.

21. The lubricant of claim 20 wherein the solution is sterile.

22. The lubricant of claim 20 wherein the mixture comprises not more than about 10% by volume of NNL-690 and not less than about 90% by volume of mineral oil.

23. The lubricant of claim 20 wherein the NNL-690 comprises a liquid hydrocarbon boundary and corrosion inhibitor.

24. The product made by the process of claim 16.

25. The product made by the process of claim 17.

26. The product made by the process of claim 18.

27. The product made by the process of claim 19.

28. The process of claim 16 further comprising the step of:

mixing vitamin E with the NNL-690 and pharmaceutical grade mineral oil.

29. The lubricant of claim 20 further comprising:

vitamin E as a rust inhibitor.

30. The product made by the process of claim 28.

* * * * *

UNITED STATES PATENT AND TRADEMARK OFFICE
CERTIFICATE OF CORRECTION

PATENT NO. : 5,520,882
DATED      : May 28, 1996
INVENTOR(S) : Kenneth R. Brown

It is certified that error appears in the above-indentified patent and that said Letters Patent is hereby corrected as shown below:

On the title page, item [57]
In the Abstract, Column 2, Line 14 after"boundary lubricant" delete ";".

In the Specification, Column 5, Line 13 after"handpiece 10 right side"delete "18".

Signed and Sealed this

Nineteenth Day of November, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,520,882
DATED : May 28, 1996
INVENTOR(S) : Kenneth R. Brown

It is certified that error appears in the above-indentified patent and that said Letters Patent is hereby corrected as shown below:

column 2, lines 53-54, after "heated" delete "at about $225^0$ F. for about one hour or".

column 2, line 54 after "until" insert --it is hygienic, that is,---.

Signed and Sealed this

Thirty-first Day of December, 1996

Attest:

BRUCE LEHMAN

*Attesting Officer*                *Commissioner of Patents and Trademarks*